United States Patent
Chuang et al.

(10) Patent No.: US 6,852,815 B1
(45) Date of Patent: Feb. 8, 2005

(54) CONDITIONING/STYLING TETRAPOLYMERS

(75) Inventors: Jui-Chang Chuang, Wayne, NJ (US); Janusz Jachowicz, Bethel, CT (US); Thomas Winkler, Maywood, NJ (US); Allen J. Krauss, Clifton, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/848,101

(22) Filed: May 18, 2004

(51) Int. Cl.[7] ............................... C08F 26/08

(52) U.S. Cl. .................... 526/264; 526/307; 526/307.2; 526/307.3; 526/307.4; 526/307.7; 526/312; 526/328.5

(58) Field of Search ............................ 526/307, 307.2, 526/307.3, 307.4, 307.7, 312, 328.5, 264

(56) References Cited

U.S. PATENT DOCUMENTS

| | | | | |
|---|---|---|---|---|
| 6,190,647 B1 | * | 2/2001 | Karlen et al. ............ | 424/70.2 |
| 6,207,778 B1 | * | 3/2001 | Jachowicz et al. ......... | 526/258 |
| 6,566,473 B1 | * | 5/2003 | Prettypaul et al. ......... | 526/264 |
| 6,685,925 B2 | * | 2/2004 | Frechet et al. ........... | 424/70.16 |
| 2003/0194415 A1 | * | 10/2003 | Wang et al. | |
| 2003/0206880 A1 | * | 11/2003 | Khoshdel | |

* cited by examiner

*Primary Examiner*—Helen L. Pezzuto
(74) *Attorney, Agent, or Firm*—Walter Katz; William J. Davis

(57) ABSTRACT

What is described herein are conditioning/styling tetrapolymers of vinyl caprolactam (VCL), vinylpyrrolidone (VP), dimethylaminopropyl methacrylamide (DMAPMA) and $C_8$–$C_{24}$ alkyl quaternized dimethylaminopropyl (meth) acrylamide or methacrylic acid quaternized monomers (QDMAPMA), in a defined compositional range. Hair and skin care compositions which include these tetrapolymers exhibit advantageous low tackiness and high humidity resistance.

16 Claims, 1 Drawing Sheet

FIGURE
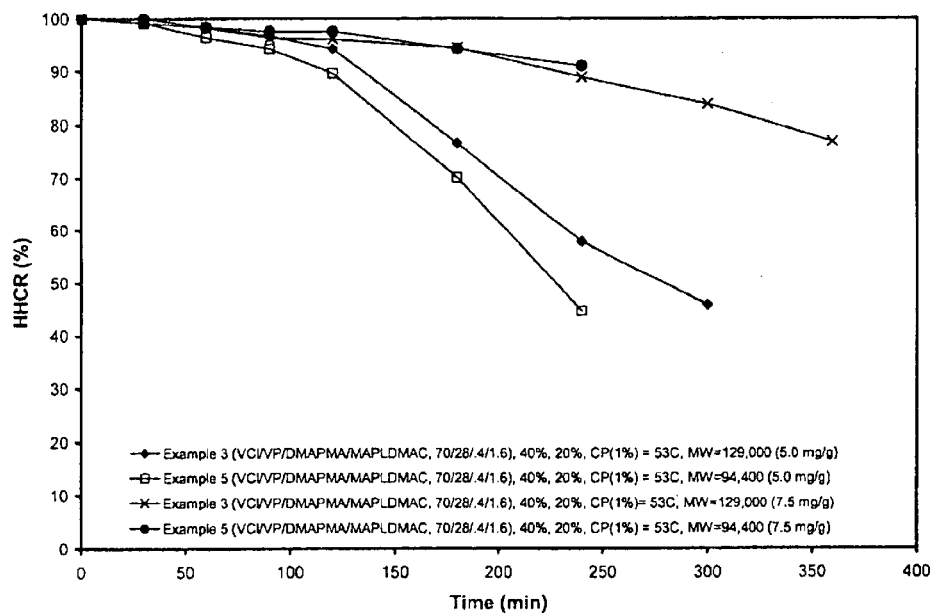

CONDITIONING/STYLING TETRAPOLYMERS

CROSS-REFERENCE TO RELATED PATENTS

This application is related to U.S. Pat. No. 6,207,778, issued Mar. 27, 2001, and assigned to the same assignee as herein.

BACKGROUND OF THE INVENTION

1. Field of the Invention

This invention relates to polymers for use in hair and skin care compositions, and, more particularly, to conditioning and styling tetrapolymers having advantageous high humidity resistance, low tackiness and a predetermined cloud point.

2. Description of the Prior Art

Copolymers of vinylpyrrolidone (VP) and dimethylaminopropyl methacrylamide (DMAPMA) have been used extensively as active components of hair and skin compositions. While these copolymers are generally suitable polymers for such products as conditioners and shampoos, it is desired to provide new polymers having improved performance characteristics in these and other personal care products.

SUMMARY OF THE INVENTION

What is described herein is a tetrapolymer of vinyl caprolactam (VCL), vinylpyrrolidone (VP), dimethylaminopropyl methacrylamide (DMAPMA) and $C_9$–$C_{24}$ alkyl quaternized dimethylaminopropyl methacrylic acid or quaternized (meth) acrylamide monomers, within a defined compositional range, for use in hair and skin care compositions, which are characterized by particularly high humidity resistance, low tackiness and advantageous high cloud points.

BRIEF DESCRIPTION OF THE DRAWING

The FIGURE is a plot of HHCR vs time for the polymers of the invention.

DETAILED DESCRIPTION OF THE INVENTION

The tetrapolymers of the invention comprise the following four monomers, namely A, B, C and D, in the compositional ranges by wt. % given below:

(A)

vinyl caprolactam
(5–85%, preferably 55–75%)

(B)

vinylpyrrolidone
(5–85%, preferably 20–40%)

(C)

(0.05–20%, preferably 0.1–5%)

where:
(C) is a derivative of acrylamide or acrylic acid; P is O or $NR_2$; $R_1$, $R_2$, $R_3$, $R_4$ are independently H or $C_1$–$C_5$ alkyl; and $R_5$ is $C_2$–$C_{16}$ alkyl alkylene;

(D)

(0.1–50%, preferably 1–10%)

where:
(D) is a quaternized derivative of an acrylamide or acrylic acid; P is O or $NR_2$; $R_1$, $R_2$, $R_3$, $R_4$ are independently H or $C_1$–$C_5$ alkyl; $R_5$ is a $C_2$–$C_{16}$ alkylene; and $R_6$ is $C_8$–$C_{24}$ alkyl; M is a halide, tosylate, phosphate or alkyl sulfate anion.

The tetrapolymers of the invention are hydrophobically-modified cationic polymers having long alkyl side-chains therein. A typical tetrapolymer (VCL-VP-DMAPMA-QDMAPMA) has the following formula:

Suitably, monomer D is prepared by quaternizing DMAPMA monomer (C) as follows:

DMAPMA + Dodecyl tosylate ⟶

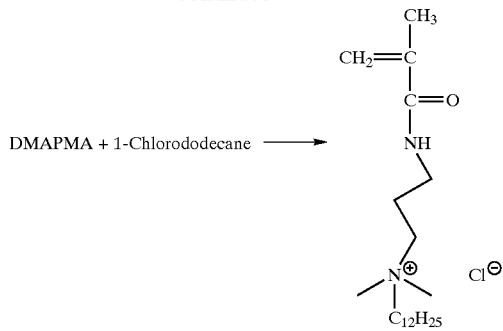

DMAPMA + 1-Chlorododecane →

In preferred embodiments of the invention,

C is dimethylaminopropyl methacrylamide, and

D is a $C_{12}$–$C_{18}$ alkyl quaternized derivative of an acrylic acid or acrylamide; preferably a $C_{12}$ alkyl quaternized monomer; the weight average molecular weight of the tetrapolymer is about 50,000 to 400,000; preferably 100,000 to 250,000; it is water soluble or water dispersible; and forms a clear, humidity resistant, hydrophobic film when cast upon a support surface; which is surface active and hydrolytically stable; and is a homogeneous tetrapolymer.

Cosmetic compositions of advantageous properties including about 0.1 to 10% by weight of the tetrapolymer can be prepared conveniently in this invention, which can include other cationic, anionic, non-ionic or amphoteric polymers, in styling formulations, and also include cationic, anionic, nonionic or amphoteric surfactants and other conventional conditioning agents. They ma also comprise protecting agents such as water-soluble, water-insoluble, or oil soluble UV filters, pigments, antiradical agents, antioxidants, vitamins and pro-vitamins. Other cosmetically acceptable additives which can be included in the composition of the invention, are fixing agents, oxidizing agents, reducing agents, dyes, cleaning agents, thickeners, perfumes, pearlizing agents, stabilizers, pH adjusters, filters, preservatives, hydroxyl acids, cationic and nonionic polyether associative polyurethanes, silicones such as aminodimethicones, dimethicones, ethoxy or propoxylated silicones, vegetable oils, mineral oils, synthetic oils, polyols, such as glycol or glycerol, aliphatic alcohols, bleaching agents and sequestrants.

Preferably, the homogeneous tetrapolymers of the invention are made according to the method described by Kou-Chang Liu et al. in U.S. Pat. No. 5,626,836 which is a solution polymerization in a suitable solvent, i.e. an ethanol and water mixture.

The tetrapolymer of the invention can be prepared at various molecular weights depending on the presence of chain transfer agents in the polymerization medium. In a mixed solvent system, e.g. 10–30% EtOH-70–90% water, a molecular weight in the range of about 50,000 to 300,000 is typical. High molecular weight polymers are more appropriate for applications in hair mousses, gels and lotions, while low molecular weight polymers are more suitable for hair sprays. For molecular weights of about 50,000 to 250,000 Daltons, a 15–30% ethanol –70–85% water solvent system is preferred.

The presence of a long alkyl chain in the copolymer structure, achieved by incorporation of DMAPMA $C_{12}$ quat chloride monomer, lowers the hydrophilicity of the polymer and improves its tactile properties (less tackiness).

An advantage of using the monomeric quat is that it also increases the cloud point of the vinyl caprolactam containing copolymers. Cloud point is the temperature at which the polymer precipitates from the solution forming dispersions, precipitates, or multiphase dispersions. Typically polymer solutions are characterized by Lower Critical Solution Temperature above which the polymer precipitates out of the solution. For example, a homopolymer of poly(vinyl caprolactam) is characterized by a cloud point of 34° C. Homopolymer of poly(vinyl pyrrolidone) is characterized by a cloud point above 100° C. The prepared tetrapolymers co(VCL-VP-DMAPMA-$C_{12}$ quat-DMAPMA chloride) are characterized by desirable cloud points in the range from 40° C. to 70° C., preferably in the range from 50° C. to 60° C. In cosmetic applications it is desirable to employ polymers with cloud points above 50° C. since its stability test is typically performed at this temperature. Accordingly, if a polymer is characterized by a cloud point lower than 50° C., a formulation containing such a material may be deemed unstable. Higher amounts of VP and lower amounts of VCL in the tetramer provide polymers with a higher cloud point. On the other hand, polymer hold, a key property for hair fixatives, which indicates the ability of polymer to hold hair at high humidities, increases by lowering the content of VP. Accordingly, copolymers containing 65% VCL are characterized by good hold, and a cloud point in the range 47–50° C. Further, adding 2–10% DMPMA-$C_{12}$ quat chloride to the copolymer composition will increase the cloud point by 2–10° C. making it acceptable for cosmetic applications.

The co(VCL-VP-DMAPMA-$Cl_2$ quat-DMAPMA chloride) polymer, with an appropriate molecular weight, typically 50,000–250,000, and compositions with a high content of VCL (up to 75%) and a low content of DMAPMA-$C_{12}$ quat, (up to 5%) can be employed as water-based hairspray polymers. A high content of VCL assures good humidity resistance, while low levels of DMAPMA-$C_{12}$ quat chloride provides good tactile properties, an improvement in hold, and an increase in the cloud point, while not causing excessive foaming of the product during application.

A preferred composition is 70/28/0.4/1.6 prepared at 25–40% solids in 20–80% ethanol-water, GPC weight-averaged molecular weight 110,000; cloud point (cP 1%) 53.5° C.

The co(VCL-VP-DMAPMA-$C_{12}$ quat-DMAPMA chloride) polymer of the invention also provides a conditioning effect to hair by altering its hair feel and hair friction.

N-oxide copolymers of the invention compositions are made by treating the copolymers with a stoichiometric amount of hydrogen peroxide with respect to the DMAPMA. The advantage of such materials is improved odor, color and enhanced compatibility with anionics.

The invention will now be described by reference to the following examples.

EXAMPLE 1

Preparation of Methacryloylaminopropyl Lauryl-Dimethyl Ammonium Chloride (MAPLDMAC)

A mixture of 350 g of DMAPMA and 280 g of chlorododecene (1.5:1) was stirred with 111.2 g of water (15%) and 6 drops of concentrated sulfuric acid. The reaction mixture was heated up to 95° C. and air was bubbled through it. The conversion was followed by chloride titration. After 24 hours the reaction was completed and the mixture was cooled off. The product is water miscible and is a mixture of 15.0% water; 69.1% MAPLDMAC and 15.9% DMAPMA. It was further used in polymerization without purification.

EXAMPLE 2

Tetrapolymer of VCL/VP/DMAPMA/DMAPMAA-$C_{12}$ Cl Quat (65/31/0.8/3.2), 33.3% Solids in 10/90 Ethanol/Water 360 g of water, 40 g of ethanol, and 6 drops of a 20% aqueous ammonium hydroxide solution were loaded into a 1-l jacketed kettle, The mixture was heated to 78° C. under a nitrogen purge with stirring at 200 rpm. Meanwhile, a pump was filled with a mixture of 130 g VCL, 62 g VP, and 9.4 g 1-chlorododecane quaternized DMAPMA mix (Example 1) consisting of 6.5 g DMAPMA-$C_{12}$ quat chloride, 1.5 g DMAPMA and 1.4 g water. At t=0, 0.20 g of Luperox® 575 (t-amyl peroxyhexanoate initiator) was added to the kettle, then the contents of the pump were emptied into the kettle at a constant rate over the next 3 hours. Additional shots of Luperox® 575 were added at t=1, 2 hours (0.20 g each) and t=4, 7 hours (0.40 g each). After the last initiator addition, the kettle was kept stirring at 78° C. for the next 10 hours. After cooling, the reactor contents (clear viscous copolymer solution) were discharged into a glass bottle.

The product was an aqueous alcoholic solution of a homogeneous tetrapolymer of VCL, VP, DMAPMA and MAPLDMAC of a predetermined composition indicative of the relative amounts of each monomer used in the process and was substantially free of any residual homopolymer or copolymer. The yield of the tetrapolymer product was substantially quantitative.

N-oxide copolymers of the invention compositions are made by treating the copolymers with a stoichiometric (or 1.5–5 fold excess, by moles) amount of hydrogen peroxide with respect to the DMAPMA.

EXAMPLES 3–10

Tetrapolymers of VCL/VP/DMAPMA/ MAPLDMAC

Tetrapolymerizations of VCL/VP/DMAPMA/ MAPLDMAC and its N-oxide derivative were carried out by following the same procedure as described in Example 2. The products and their properties are shown in the Table below.

TABLE

| Ex. | Composition | Solids (%) w/w | EtOH/$H_2O$ | MW | CP (1%) |
|---|---|---|---|---|---|
| 3 | 70/28/0.4/1.6 | 40 | 20/80 | 129,000 | 53.5 |
| 4 | 70/28/0.4/1.6 | 40 | 25/75 | 71,600 | 53 |
| 5 | 70/28/0.4/1.6 | 40 | 25/75 | 94,400 | 53 |
| 6 | 70/24/4.4/1.6 | 25 | 10/90 | 212,000 | 55 |
| 7 | 75/23/1.6/0.4 | 25 | 10/90 | 287,000 | 52 |
| 8 | 65/34/0.8/0.2 | 25 | 10/90 | 196,000 | 58 |
| 9 | 65/33/1.6/0.4 | 25 | 10/90 | 239,000 | 57 |
| 10 | 65/33/2.4/0.6 | 33 | 10/90 | 409,000 | 55 |

Composition: VCL/VP/DMAPMA/DMAPMA$^\oplus$-$C_{12}H_{25}Cl^\ominus$ or VCL/VP/DMAPMA-O/DMAPMA$^\oplus$-$C_{12}H_{25}Cl^\ominus$ (Exs. 3–5)
CP (1%) - Cloud point for 1% solution

EXAMPLE 11

Conditioning Cream Rinse Formulation

| Raw material | % w/w |
|---|---|
| Phase A | |
| NaEDTA | 0.1 |
| DI Water | 90.3 |
| Polymer (from Example 6) (25%) | 2.5 |
| Phase B | |
| Cetearyl alcohol | 4 |
| Glyceryl stearate | 1.5 |
| PEG-20 stearate | 1.5 |
| Phase C | |
| Diazolidinyl urea/IPBC (Germall Plus ISP) | 0.1 |

Instructions

Heat Part A to 60° C. with moderately slow stirring. Melt Part B and add slowly to part A with stirring until the mixture appears well mixed and homogenous. Continue slow stirring and allow solution to cool to an ambient temperature. Add Part C while stirring.

EXAMPLE 12

Hair moisturizer

| Raw material | % w/w |
|---|---|
| Phase A | |
| Isoeicosane | 28.00 |
| Lanolin | 7.00 |
| Beeswax | 5.00 |
| Petrolatum | 3.00 |
| Sorbitan oleate | 2.00 |
| Octyl methoxycinnamate | 2.50 |
| Propylparaben | 0.15 |
| Phase B | |
| Deionized water | 49.15 |
| Polymer (from Example 6) | 1.0 |
| Sodium borate | 0.90 |
| Propylene glycol | 0.75 |
| Methylparaben | 0.30 |
| Panthenol | 0.25 |

Combine A and heat to 75° C. while stirring. Separately, combine Phase B, heat it to 75° C. Add B to A using rapid agitation and then cool to room temperature.

EXAMPLE 13

Conditioning Shampoo Formulation

| Raw material | % w/w |
|---|---|
| Phase A | |
| Ammonium lauryl sulfate | 15.0 |
| Sodium lauryl sulfate | 15.0 |
| Cocamidopropyl betaine | 8.0 |
| Deionized water | 58.8 |
| Polymer (from Example 9) | 1.0 |
| Phase B | |
| Lauramide DEA | 2.0 |
| Phase C | |
| Diazolidinyl urea/IPBC (Germall Plus, ISP) | 0.2 |

Instructions

Heat Part A to 60° C. with slow stirring for approximately 72 hr. or until solution becomes transparent. At the same time, heat Part B to 55° C. and add Part B to Part A while continuously stirring. Remove temperature source. Once the resulting solution has reached 45° C., add Part C. Continue to stir (slowly) until the target solution has cooled to an ambient temperature.

EXAMPLE 14

Conditioners and shampoo formulations were tested under actual use conditions in comparison with similar formulations with known polymers and surfactants. Trained panelists were employed to assess characteristics of treated hair in terms of combing ease, luster, residue and static charge. In addition to this instrumental methods such as combing analysis and High Humidity Curl Retention were employed. It was found that the products based on polymers of the present invention are characterized by excellent wet combing, excellent dry feel and softness and excellent wet feel.

EXAMPLE 15

Styling Lotion

A styling lotion formulation was prepared in aqueous solution using 1–3% by weight of the tetrapolymer from Example 3 or Example 5 and 0.1% preservative.

EXAMPLE 16

High Humidity Curl Retention Analysis (HHCR)

Hair lotions prepared in Example 15 were employed to treat 2 g hair tresses, which were then curled on rollers, dried at 40° C. and subjected to HHCR analysis at 90% RH and 27° C. The results of such an experiment for polymer samples of Example 3 and Example 5 are presented in the Figure.

The results show very good HHCR for hair treated with 7.5 mg polymer/1 g of hair and moderately high values for a lower dose of 5 mg polymer/1 g of hair. It should be noted that the test was carried out by using very thick Chinese hair with an average cross-sectional of 0.0075 mm$^2$.

EXAMPLE 17

| Nonaerosol Styling Spray | |
|---|---|
| Raw material | % w/w |
| DI Water | 92.3 |
| Polymer (from Example 5) (40%) | 7.5 |
| Diazolidinyl urea/IPBC (Germall Plus, ISP) | 0.2 |

The product was tested by measuring pump spray distribution patterns and HHCR. A product according to a composition shown above was found to produce a good spray pattern with fine particles (DV50 equal to 81 μm), and good HHCR at a treatment dose of 7.5 mg polymer per g of hair.

EXAMPLE 18

| Transparent Hair Gel Preparation of Carbopol ® 940 slurry | |
|---|---|
| Raw material | % w/w |
| Carbopol ® 940 (Noveon) | 2 |
| DI Water | 98 |

Disperse Carbopol® 940 in water and mix until air bubbles are released and the slurry becomes homogenous (translucent, off-white).

| Preparation of a Hair Gel | |
|---|---|
| Raw material | % w/w |
| Phase A | |
| Carbopol 940 slurry | 25 |
| DI water | 46.3 |
| Phase B | |
| Polymer (from Example 3) (40%) | 2.5 |
| DI water | 25 |
| Phase C | |
| AMP-95 (Angus, 95% soln.) | 1 |
| Diazolidinyl urea/IPBC (Germall Plus, ISP) | 0.2 |

Prepare Phase A and Phase B. Combine Phase A and Phase B. Adjust pH to 7 by using Phase C.

A hair gel prepared in this way was tested on hair and showed good characteristics in terms of hair shine, stiffness, curl snap, comb drag, residue on comb, residue on hair after combing, manageability and static charge. It has also shown 94% High Humidity Curl Retention after 4 hours at 90% RH.

EXAMPLE 19

| Hair Mousse | |
|---|---|
| Raw material | % w/w |
| Phase A | |
| Polymer of Example 7 | 5.0 |
| Laureth-23 | 0.5 |
| Cetrimonium chloride | 0.1 |
| Oleth-10 | 0.2 |
| Citric acid (25%) | 0.2 |
| DI Water | 78.0 |
| Phase B | |
| Hydrofluorocarbon 152a (Dymel 152a, DuPont) | 10.0 |
| Isobutane (A-31, Aeropres) | 6.0 |

Combine ingredients for Phase A, mixing well between each addition. Adjust pH to 6 with citric acid. Fill the concentrate into cans, vacuum crimp and charge with B.

Styling mousse formulations based on the polymers of the present invention are characterized by high stiffness, high humidity resistance and good dry and wet feel.

EXAMPLE 20

Hair Bleach
Bleaching Powder

| Raw material | % w/w |
|---|---|
| Potassium persulfate | 33 |
| Sodium persulfate | 37 |
| Sodium metasilicate | 12 |
| Ammonium chloride | 6 |
| EDTA | 1 |
| Sodium dioctylsulfosuccinate/sodium benzoate | 1 |
| Calcium stearate | 1 |
| Silica | 9 |

40 g of the above anhydrous composition was mixed with 80 g of the following aqueous composition:

Developer/Oxidizer

| Raw material | % w/w |
|---|---|
| Cetearyl alcohol/Ceteareth-30 | 3.0 |
| NaEDTA | 0.15 |
| Hydrogen peroxide (35%) | 22.95 |
| Phosphoric acid | qs to pH 2.5 |
| Polymer of Example 6 (25%) | 2.5 |
| DI water | qs 100% |

A bleaching cream was obtained, which applied and left for 45 minutes, permitted homogeneous bleaching of dark natural hair characterized by good, conditioned feel of hair after the procedure.

EXAMPLE 21

Permanent Wave Composition
Reducing composition:

| Raw material | % w/w |
|---|---|
| Thioglycolic acid | 9.2 |
| Arginine | 15 |
| Ammonia (20%) | 9.3 |
| Ammonium carbonate | 4.5 |
| Cocoylamidopropylbetaine/glycerol monolaurate (25/5) in 30% aqueous solution | 1.3 |
| Isostearyl alcohol | 12 |
| Polymer of Example 4 | 2.5 |
| NaEDTA | 0.4 |
| Perfume | 0.4 |
| DI water | qs 100 |

This reducing composition was applied to a lock of moist hair wound onto a curler beforehand 9 mm in diameter. After 10 minutes of waiting it was rinsed abundantly with water. The following oxidizing composition was then applied:

Oxidizing composition:

| Raw material | % w/w |
|---|---|
| Hydrogen peroxide (35%) | 5.7 |
| NaEDTA | 0.1 |
| Phosphoric acid | qs pH 2.5 |
| DI water | qs 100 |

After 10 minutes of waiting, the lock was abundantly rinsed again. The hair was then unwound from the curler and dried. Panel examination of hair tresses has shown that they are characterized by good tactile properties.

EXAMPLE 22

Hair Relaxer

| Raw material | % w/w |
|---|---|
| Phase A | |
| Deionized water | 53.5 |
| Propylene glycol | 2.00 |
| Polymer of Example 6 | 2.5 |
| Phase B | |
| Emulsifying wax (Polawax) | 15.0 |
| Petrolatum | 8.00 |
| Hydrogenated polyisobutene | 10.0 |
| Phase C | |
| Sodium Hydroxide, 25% soln. | 8.00 |
| Phase D | |
| Propylene glycol (and) diazolidinyl urea (and) methylparaben (and) propylparaben | 1.00 |

Heat premixed A and B separately to 75° C. and add B to A with rapid mixing. Cool to 40° C. before adding C and D.

The composition can be employed for straightening very curly hair.

Several examples of skin care products which can be prepared use the polymers of the present invention.

EXAMPLE 23

Oxidative Hair Colorant

| Raw Material | % w/w |
|---|---|
| Coloring lotion | |
| Deionized H$_2$O | 66.10 |
| C14–15 Pareth-10 | 10.0 |
| C12–15 Pareth-3 | 10.0 |
| NH$_4$OH | 4.2 |
| Ethanolamine | 3.6 |
| Dyes | 1.4 |
| 0.35% p-phenylenediamine | |
| 0.35% 2-methylresorcinol | |
| 0.25% resorcinol | |
| 0.25% p-aminophenol | |
| 0.10% 4-amino-2-hydroxytoluene | |
| 0.05% 1-Naphthol | |
| 0.05% N,N-bis-(2-hydroxyethyl)-p-phenylenediamine sulfate | |
| Dimethylpabamidopropyl Lauridimonium Tosylate | 1.0 |
| Polymer of Example 6 | 2.5 |
| Decyl Glucoside | 0.5 |
| Na Bisulfite | 0.3 |
| L-Ascorbic Acid | 0.3 |
| NaEDTA | 0.1 |
| Developer | |
| Deionized H$_2$O | 95.4 |
| H$_2$O$_2$ (35%) | 3.0 |
| Acrylates/Steareth-20 Methacrylate Copolymer | 1.5 |
| NaEDTA | 0.1 |

Coloring lotion and developer are combined prior to hair treatment to form a coloring gel. Hair was saturated with the product and allowed to react for 30 minutes. Hair was then thoroughly rinsed and dried. It was evaluated by panel, which has shown good hair characteristics in terms of color, luster, surface residue, feel and mechanical properties.

EXAMPLE 24

Skin Protectant/Sunscreen

| Raw material | % w/w |
|---|---|
| Phase A | |
| Deionized water | 60.35 |
| Carbomer 934 | 0.20 |
| Propylene glycol | 6.25 |
| Cellulose gum | 0.10 |
| Polymer of Example 7 | 5.0 |
| Methyl paraben | 0.20 |
| Phase B | |
| Isoeicosane | 12.00 |
| Isooctahexacontane | 4.00 |
| Steareth-2 | 2.90 |
| Steareth-21 | 2.10 |
| Propylparaben | 0.10 |
| Octyl methoxycinnamate | 6.00 |
| Phase C | |
| Triethanolamine | 0.50 |
| Phase D | |
| Fragrance | 0.30 |

Disperse Phase A and heat to 70–72° C. In a separate vessel combine Phase B and heat to 72–75° C. Mix (A) and (B) and add (C). Mix and cool to 40° C. and add (D).

EXAMPLE 25

Skin Moisturizer

| Raw material | % w/w |
|---|---|
| Phase A | |
| Deionized water | 81.9 |
| Hydroxyethyl cellulose | 1.00 |
| Polymer of Example 7 | 2.5 |
| Sorbitol | 1.00 |
| Phase B | |
| Stearic acid | 3.00 |
| Glyceryl stearate (and) PEG-100 stearate | 2.50 |
| PEG-75 lanolin oil | 0.50 |
| Cetyl alcohol | 0.50 |
| Phase C | |
| Collagen amino acids | 5.00 |
| Phase D | |
| Dimethicone | 1.00 |
| Propylene glycol (and) diazolidinyl urea (and) methylparaben (and) propylparaben | 1.00 |
| Fragrance | 0.10 |

Heat water to 80° C., sprinkle hydroxyethyl cellulose into water with constant agitation, add the rest of Phase A and mix until clear. Melt and mix Phase B ingredients and mix until homogenous. Add slowly Phase B to Phase A. Cool to room temperature. Slowly add collagen amino acids and mix until smooth. Add D ingredients and mix until uniform.

EXAMPLE 26

Anti-Wrinkle Treatment Cream

| Raw material | % w/w |
|---|---|
| Phase A | |
| Sodium behenoyl lactylate | 2.00 |
| Cetearyl alcohol | 3.00 |
| Glyceryl stearate | 2.60 |
| Isopropyl palmitate | 6.00 |
| Sunflower seed oil | 6.00 |
| Phase B | |
| Deionized water | 66.20 |
| Glycein | 3.00 |
| Polymer of Example 7 | 5.0 |
| Phase C | |
| DMDM hydantoin | 0.20 |
| Sodium lactate (and) lecithin | 6.00 |

Mix A with mixing, heat to 80° C. Heat B to 80° C. Add A to B with vigorous stirring. When homogenous, cool to 35° C. and add C.

EXAMPLE 27

Body Wash

| Raw material | % w/w |
|---|---|
| Phase A | |
| Deionized water | qs |
| Sodium cocoamphoacetate | 10.00 |
| Polymer of Example 6 | 2.5 |
| Citric Acid | 0.10 |
| Phase B | |
| Sodium methyl oleoyl taurate | 1.50 |
| Glycol distearate | 1.50 |
| Ceteareth-20 | 0.30 |
| Glycerin | 1.00 |
| Phase C | |
| Sodium laureth sulfate | 45.0 |
| Phase D | |
| Preservative and fragrance | qs |

Combine A by first dispersing the polymer and then adding the rest of ingredients, heat to 75° C. Combine B at the same temperature. Add B to A while mixing. Add C and adjust viscosity with NaCl. Cool to 35° C. and add preservative and fragrance.

EXAMPLE 28

Skin Tightening Gel

| Raw material | % w/w |
|---|---|
| Phase A | |
| Deionized water | 85.3 |
| Carbomer 934 | 0.40 |
| Butylene glycol | 1.0 |
| Propylene glycol | 1.0 |
| Glycerine | 0.5 |
| Cellulose gum | 1.0 |
| Polymer of Example 10 (33%) | 9.0 |

-continued

Skin Tightening Gel

| Raw material | % w/w |
|---|---|
| Phase B | |
| Propylene Glycol (and) Diazolidinyl Urea (and) Methyl Paraben (and) Propylparaben | 0.5 |
| Phase C | |
| Triethanolamine | 1.00 |
| Phase D | |
| Fragrance | 0.30 |

Disperse Phase A and mix it until homogenous. Add (B), (C), and (D) and mix until homogenous and clear.

While the invention has been described with particular reference to certain embodiments thereof, it will be understood that changes and modifications may be made which are within the skill of the art. Accordingly, it is intended to be bound only by the following claims, in which:

What is claimed is:

1. A hydrophobically-modified cationic tetrapolymer consisting essentially of the following monomers in wt. %;

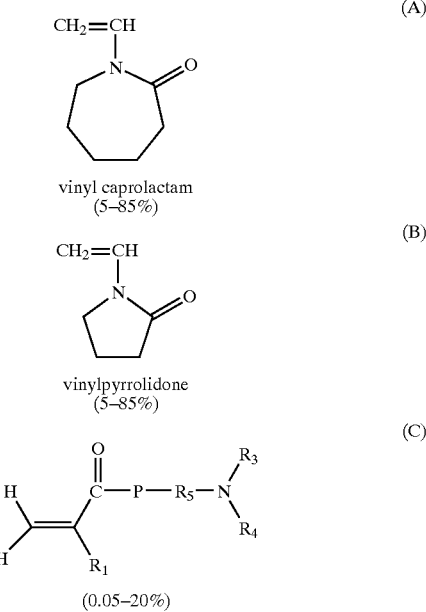

where:

P is O or $NR_2$; $R_1$, $R_2$, $R_3$, $R_4$ are independently H or $C_1$–$C_5$ alkyl; $R_5$ is $C_2$–$C_{16}$ alkylene; and

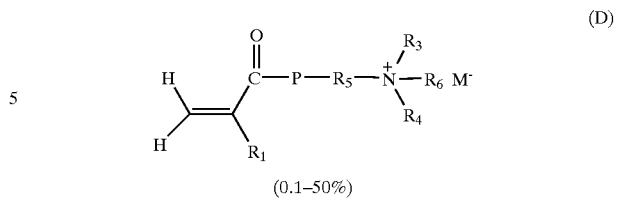

(0.1–50%)

where:

P is O or $NR_2$; $R_1$, $R_2$, $R_3$, $R_4$ are independently H or $C_1$–$C_5$ alkyl; $R_5$ is a $C_2$–$C_{16}$ alkylene; $R_6$ is $C_8$–$C_{24}$ alkyl; and M is a halide, tosylate or phosphate anion.

2. A tetrapolymer according to claim 1 wherein:
   (C) is dimethylaminopropyl methacrylamide, and
   (D) is a $C_8$–$C_{18}$ alkyl quaternized derivative of an acrylamide or acrylic acid.

3. A tetrapolymer according to claim 2 wherein (A) is about 55–75%; (B) is about 20–40%; (C) is about 0.1–5%; and (D) is about 0.5–10%.

4. A tetrapolymer according to claim 2 wherein (D) is a $C_{12}$ alkyl quaternized monomer.

5. A tetrapolymer according to claim 1 wherein the weight average molecular weight is 50,000 to 400,000.

6. A tetrapolymer according to claim 5 wherein said molecular weight is 100,000 to 250,000.

7. A tetrapolymer according to claim 2 which is water soluble or water dispersible.

8. A tetrapolymer according to claim 1 which forms a clear, humidity resistant, hydrophobic film when cast upon a support surface.

9. A tetrapolymer according to claim 1 which is surface active and hydrolytically stable.

10. A tetrapolymer according to claim 1 which is a homogeneous tetrapolymer.

11. A tetrapolymer according to claim 1 which (C) is an N-oxide derivative.

12. A cosmetic composition including about 0.1 to 10% by weight of the tetrapolymer of claim 1.

13. A cosmetic composition according to claim 12 which is a hair or skin care product.

14. A cosmetic composition according to claim 12 which is a skin tightening product.

15. A method of making the tetrapolymer of claim 1 which comprises polymerizing said monomers in an alcohol-water solvent mixture.

16. A method according to claim 15 wherein said solvent mixture is 10–30 wt % ethanol and 70–90 wt % water.

* * * * *